US010334869B2

(12) United States Patent
Collins et al.

(10) Patent No.: US 10,334,869 B2
(45) Date of Patent: Jul. 2, 2019

(54) METHOD FOR INCREASING CONCENTRATION OF AVENANTHRAMIDES IN OATS

(75) Inventors: Frank William Collins, Ottawa (CA); Vernon Douglas Burrows, Nepean (CA)

(73) Assignee: HER MAJESTY THE QUEEN IN RIGHT OF CANADA, AS REPRESENTED BY THE MINISTER OF AGRICULTURE AND AGRI-FOOD, Saskatchewan (CA)

( * ) Notice: Subject to any disclaimer, the term of this patent is extended or adjusted under 35 U.S.C. 154(b) by 216 days.

(21) Appl. No.: 13/259,447

(22) PCT Filed: Mar. 25, 2010

(86) PCT No.: PCT/CA2010/000458
§ 371 (c)(1),
(2), (4) Date: Dec. 12, 2011

(87) PCT Pub. No.: WO2010/108277
PCT Pub. Date: Sep. 30, 2010

(65) Prior Publication Data
US 2012/0082740 A1 Apr. 5, 2012

Related U.S. Application Data

(60) Provisional application No. 61/163,975, filed on Mar. 27, 2009.

(51) Int. Cl.
*A61K 36/899* (2006.01)
*A23K 20/111* (2016.01)
*C12P 13/02* (2006.01)
*A23L 7/10* (2016.01)
*A23L 7/25* (2016.01)
*A23L 33/105* (2016.01)

(52) U.S. Cl.
CPC ............. *A23K 20/111* (2016.05); *A23L 7/197* (2016.08); *A23L 7/25* (2016.08); *A23L 33/105* (2016.08); *A61K 36/899* (2013.01); *C12P 13/02* (2013.01)

(58) Field of Classification Search
None
See application file for complete search history.

(56) References Cited

U.S. PATENT DOCUMENTS

2005/0042243 A1* 2/2005 Redmond et al. ............ 424/401
2006/0280851 A1* 12/2006 Pike ............................ 426/533
2013/0183405 A1* 7/2013 Chatel ...................... A23L 2/02
426/28
2016/0095335 A1* 4/2016 Chu ........................ A23L 7/115
514/563

FOREIGN PATENT DOCUMENTS

WO 00/67626 A2 11/2000

OTHER PUBLICATIONS

Bryngelsson et al. (2003) Cereal Chemistry, vol. 80, No. 3, pp. 356-360.*
Bratt et al. (2003) J. Agric. Food Chem. 51, 594-600.*
Bryngelsson et a. (2002) J. Agric. Food Chem. 50, 1890-1896.*
Skoglund et al. (2008) J. Cereal Sci. 48, 294-303.*
Atanasoff et al. (1920) J. Agric. Res. vol. XVIII, No. 7, 379-390.*
Skoglung et al. (2008) J. Cereal Res. 48: 294-303.*
Tian et al. (2010) Food Chemistry 119: 1195-1200.*
Decision of Refusal for Japanese Patent Application No. 2012-501095, dated May 22, 2014, pp. 1-4.
Ishihara et al., "Study on biosynthesis-inducing mechanism in avenanthramides," Journal of the Japan society for bioscience biotechnology and agrochemistry, Aug. 2004, vol. 29, No. 3, pp. 227-233.
Miyagawa et al., "Avenanthramides in oats," Journal of the Japan society for bioscience biotechnology and agrochemistry, May 1998, vol. 72, No. 5, pp. 669-672.
Dimberg, L.H. et al., "Avenanthramides—A group of phenolic antioxidants in oats," Cereal Chemistry, vol. 70, No. 6, pp. 637-641 (1993).
Bryngelsson, S. et al., "Effects of commercial processing on levels of antioxidants in oats (*Avena staiva* L.)," J. Agric. Food Chem., vol. 50, pp. 1890-1896 (2002).
Bryngelsson, S. et al., "Levels of avenanthramides and activity of hydroxycinnamoyl-CoA:hydroxyanthranilate N-hydroxycinnamoyl transferase (HHT) in steeped of germinated Oat samples," Cereal Chemisry, Vo. 80, No. 3, pp. 356-360 (2003).
Collins, F.W., "Oat Phenolics: Avenanthramides, Novel Substituted N-Cinnamoylanthranilate alkaloids from oat groat and hulls," J. Agric. Food Chem., vol. 37, pp. 60-66 (1989).
Kaukovirta-Norja, A. et al., "Germination: a means to improve functionality of oats," Agricultural and Food Science, vol. 13, pp. 100-112 (2004).
Xu, J.G. et al., "Dynamic Changes in phenolic compounds and antioxidant activity in oats (*Avena nuda* L.) during steeping and germination," J. Agric. Food Chem., vol. 57, pp. 10392-10398 (Oct. 2009).
Collins, F., "Avenanthramides in oats: A new method of producing whole oats and oat ingredients with greatly elevated avenathramide levels," Cereal Foods World Supplement, AACC International Annual Meeting Abstracts, vol. 54, No. 4, A18 (Sep. 13-16, 2009).

(Continued)

*Primary Examiner* — Christopher R Tate
*Assistant Examiner* — Russell G Fiebig
(74) *Attorney, Agent, or Firm* — McDonnell Boehnen Hulbert & Berghoff LLP

(57) ABSTRACT

Methods for increasing the levels of avenanthramides in oats through false malting is disclosed. Oats are first subject to induction or enhancement of a secondary dormancy, and then malted for up to 5 days at an elevated temperature. The malted but not germinated oats are then dried and used as is, or further processed or milled to produce food, feed, nutraceutical or personal care products and ingredients. Methods are also provided for rendering non-dormant oats dormant and thus suitable for false malting.

9 Claims, 7 Drawing Sheets

(56) References Cited

OTHER PUBLICATIONS

Collins, F., "Avenanthramides in oats: A new method of producing whole oats and oat ingredients with greatly elevated avenathramide levels," Cereal Science Knowledge Database, America Association of Cereal Chemists, (AACC), direct submission (Jan. 2010).
Li B et al, Oct. 1997, "Genetic and Molecular Control of Seed Dormancy", Trends in Plant Science, Elsevier Science Ltd., vol. 2, No. 10, pp. 384-389.
Meydani, M, 2009, "Potential Health Benefits of Avenanthramides of Oats", Nutrition Reviews, vol. 67(12), pp. 731-735.
Skoglund, M. et al., 2007, "Avenanthramide content and related enzyme activities in oats as affected by steeping and germination", Journal of Cereal Science (2007), doi: 10.1016/j.jcs.2007.09.010.
Tsuru, Notification of Reasons for Refusal (English translation), Japanese Patent Application No. 2012-501095, dated Sep. 2, 2013 (Third Patent Examination Department, Biotechnology, Japan Patent Office).
Adkins & Ross, "Studies in Wild Oat Seed Dormancy: I. The role of ethylene in dormancy breakage and germination of wild oat seeds (*Avena fatua* L)," Plant Physiol., 67(2):358-62 (1981).
Berrie, "Possible Role of Volatile Fatty Acids and Abscisic Acid in the Dormancy of Oats," Plant Physiol., 63 (4):758-64 (1979).
Chen & Varner, "Respiration and Protein Synthesis in Dormant and After-ripened Seeds of *Avena fatua*," Plant Physiol., 46(1):108-12 (1970).
Fennimore et al., "A genetic model and molecular markers for wild oat (*Avena fatua* L.) seed dormancy," Theor Appl Genet., 99(3-4):711-18 (1999).
Larondelle et al., "Fructose 2,6-bisphosphate in germinating oat seeds, A biochemical study of seed dormancy" Eur. J. Biochem., 166(3):605-10 (1987).

\* cited by examiner

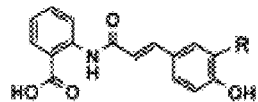

R = H  Avenanthramide D
R = OCH₃  Avenanthramide E
R = OH  Avenanthramide F

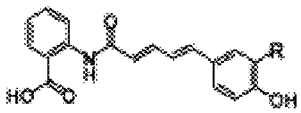

R = H  Avenanthramide L*
R = OCH₃  Avenanthramide M
R = OH  Avenanthramide N*

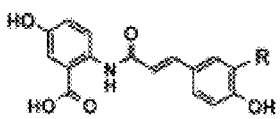

R = H  Avenanthramide A
R = OCH₃  Avenanthramide B
R = OH  Avenanthramide C

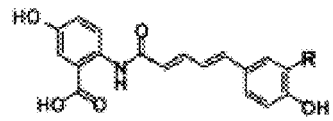

R = H  Avenanthramide O
R = OCH₃  Avenanthramide P
R = OH  Avenanthramide Q

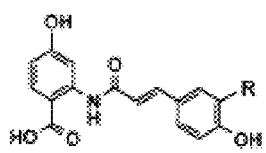

R = H  Avenanthramide G
R = OCH₃  Avenanthramide H
R = OH  Avenanthramide K

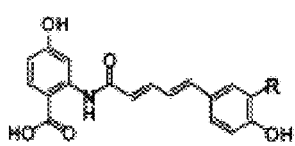

R = H  Avenanthramide R*
R = OCH₃  Avenanthramide S*
R = OH  Avenanthramide T*

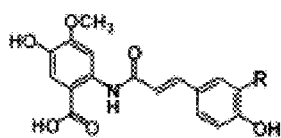

R = H  Avenanthramide X
R = OCH₃  Avenanthramide Y
R = OH  Avenanthramide Z

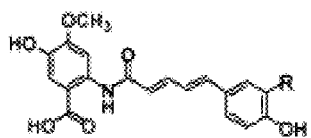

R = H  Avenanthramide U*
R = OCH₃  Avenanthramide V*
R = OH  Avenanthramide W*

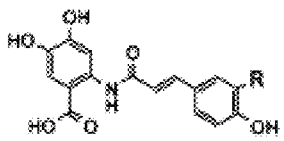

R = H  Avenanthramide AA
R = OCH₃  Avenanthramide BB
R = OH  Avenanthramide CC

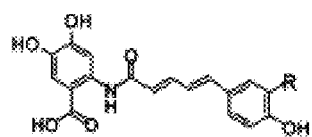

R = H  Avenanthramide OO
R = OCH₃  Avenanthramide PP
R = OH  Avenanthramide QQ

* Minor Avenanthramides identified by UV spectra and LC-MS/MS

FIG. 2

METHOD FOR INCREASING CONCENTRATION OF AVENANTHRAMIDES IN OATS

BACKGROUND OF THE INVENTION

The present invention relates to avenanthramides, and more specifically, to a method for increasing concentration of avenanthramides in oats.

Oats are unique amongst the cereals in their capacity to synthesize and store several groups of bioactive phytochemicals including avenanthramides, avenacosylates, triterpene saponins (avenacosides) and steroid saponins (avenacins).

Avenanthramides are a group of about 30 different N-aroylanthranilic acid alkaloids of the general formula depicted in FIG. 1.

Avenanthramides are antioxidants and have been shown to be bio-available in humans and other animals, to have cardiovascular health effect in vivo.

Using purified avenanthramide mixtures, it has been shown that avenanthramides are bio-available in hamsters and humans, and act synergistically with vitamin C to enhance LDL-cholesterol resistance oxidation. In another study, the pharmacokinetics of avenanthramide uptake in healthy adults was determined. Using a randomized, placebo controlled, three way crossover trial with purified avenanthramides, at two oral dose levels, approximately 60 and 120 mg, avenanthramides were bio-available and enhanced the oxidative defense system of humans, in a dose-dependent manner, as measured by plasma glutathione levels. It can be concluded that for the observed bio-activity, threshold levels of avenanthramides, approximately 30 to 60 mg from a dietary source delivery system such as a 50 g serving of oat bran, would require an oat product with about 600 to 1,200 parts per million (ppm) total avenanthramides. This is a substantially higher concentration than those currently recorded for existing oat varieties or existing oat products.

It is well known that oatmeal, usually formulated into colloidal suspensions have been used topically for hundreds of years for skin conditions such as eczema, poison ivy, insect bites, sunburn, and shingles, where inflammation is known to be the main culprit. Avenanthramides at about 10 ppm now form the core active ingredient in a number of products for personal and pet care markets worldwide due to their topical anti-irritant, anti-itch and anti-inflammatory activities.

Avenanthramides also have shown anti-cancer preventative properties in vitro. Synthetic avenanthramide C (FIG. 1; n=1, $R_1$=OH, $R_2$=H, $R_3$=OH,) at about 40 ppm has recently been shown in vitro to inhibit the proliferation of smooth muscle cells and nitric oxide production in both rat and human embryonic aorta vessel wall cultures. At concentrations of 4 to 20 ppm in this in vitro system, an avenanthramide mixture purified from VAO-6 bran significantly reduced the "stickiness" of these cells towards oxidized LDL-cholesterol and inhibited the formation of pro-inflammatory signaling molecules that promote the build-up of cholesterol-based arterial plaque. In addition, it has recently been found that purified oat avenanthramides, avenanthramide C in particular have anti-inflammatory and anti-proliferative activity against colonic cancer cell lines when treated at about the 20 to 50 ppm level, but had no effect on normal cell lines.

Avenanthramides are also potent antioxidants in vitro. It has been shown that avenanthramides are inhibitors of certain pathogenic stages of atherosclerosis (cardiovascular disease), the leading cause of morbidity and mortality in Western society. Using human aorta epithelial cell cultures, both individual avenanthramides and purified oat avenanthramide mixtures extracted from oat bran showed anti-atherogenic and anti-inflammatory bioactivity. More recently, the mechanism of the anti-inflammatory action of avenanthramides in human aortic monolayer cell cultures has been attributed to their inhibition of nuclear factor κB activation by inhibiting the phosphorylation of IκB kinase and IκK proteins, key factors in the initiation, progression and complication of atherogenesis.

Avenanthramides are present in current oat varieties at concentrations too low to elicit these benefits. From clinical evidence involving human subjects, effective minimum levels of single doses would have to be in the range of 1000 to 3000 ppm antioxidant.

However, North American and Scandinavian covered oat varieties generally contain from about 4 ppm to about 150 ppm total avenanthramides and these levels can vary widely depending on genotype, environment, crop year and location. Regardless of genotype/environment interactions, the avenanthramide content of outer layers of the grain is always higher than that of the starchy endosperm indicating avenanthramides are localized primarily in the bran fraction. Prior art cultivation efforts show levels can be increased up to about 130% of the starting levels in dry kernels.

The levels of avenanthramides in whole kernels can also be increased through physiological and/or mechanical processes. Malting is a process of soaking and germinating cereal grains to change the composition of the grain for a variety of end purposes, and has been practiced for millennia. For example, the malting process leads to the breakdown of complex carbohydrates, lipids and protein, rendering these reserve sources of sugars, fatty acids and amino acids more nutritionally available both to the grain itself, for further development of the embryonic plant, and to those organisms consuming it.

For example, it has been shown that the total amount of avenanthramides increased 150% during a 48 hours germination period. It has also been shown that total avenanthramides increased in whole oat kernels from about 90 ppm to about 110 ppm, a 27% increase, during 10 hours of steeping in tap water at 20° C. The increase in total avenanthramide levels was time and temperature dependent. With increased temperature of steeping, levels increased by as much as 50% to about 75 ppm during 10 hours of steeping. Increasing the temperature above 20° C., for example at 40° C., or prolonging steeping, for example, for 48 hours, did not result in further increases in avenanthramides. Simply initiating water imbibitions in dry kernels results in avenanthramide increases although the levels increase only marginally, and did not result in accumulation of substantial quantities.

It is apparent from the existing studies that current technologies for increasing avenanthramides through malting will not produce a malted product with sufficiently high levels of avenanthramides to elicit the desired physiological responses outlined above. Furthermore, since the malting/germination processes which produce these increases also result in a germinated oat seedling with roots, shoots and partially-depleted malted kernels, especially with malting times in excess of 2 days, the sprouted product would have limited use in any further dry fractionation/milling application due to the presence of roots, coleoptile and other anatomical modifications associated with germinated kernels. In addition, existing technologies have been developed mainly for covered oats, resulting in a sprouted grain with hulls still attached. De-hulling prior to malting by mechanical means, such as impact or compressed air de-hulling, widely used in the industry as well as the secondary "polishing" procedures, i.e. removal of trichomes located on the outside of the oat groat, may severely compromise the integrity of the intact kernel resulting in damaged kernels which is undesirable for malting. Furthermore, de-hulling and polishing of the malted product is complicated by changes in the softness and density of the malted material.

The germinated oat sprouts consisting of roots, shoots and partially-depleted malted kernels are also difficult to mill into either traditional oat products such as rolled oat flakes, oat bran or oat flour, suitable for incorporation into directly-consumable foods or for incorporation into baked foods as an ingredient.

In addition, given the strong genotype/environment interactions already observed, the possibility of producing a high avenanthramide oat through classical breeding techniques represents a long-term solution which might take many years to achieve.

Therefore, there is a need for a substantial increase of the concentration of avenanthramides in oat kernels so that the potential beneficial effects of avenanthramides such as in ameliorating cardiovascular health can be realized.

SUMMARY OF THE INVENTION

In accordance with one embodiment of the present invention there is provided a method of producing oats with an increased avenanthramide concentration by subjecting the oats in dormancy to false malting, resulting in the oats with the increased avenanthramide concentration and without germination.

Preferably, when the oats are non-dormant, the dormancy is induced.

Preferably, when the oats are non-dormant, the dormancy is enhanced.

Preferably, the oats are anaerobically steeped to induce or to enhance the dormancy.

Preferably, the oats are dry-heated before the false malting to induce the dormancy.

Preferably, the oats are dry-heated at from 30 to 40° C. for from 48 to 72 hours followed by further dry-heating at about 70° C. for from 144 to about 168 hours.

Preferably, the oats are anaerobically steeped by soaking the oats in water at from 4 to 40° C. for from 12 to 18 hours.

Preferably, the oats are anaerobically steeped in water including calcium ion.

Preferably, the oats are incubated at a temperature at from 4 to 40° C. for from 96 to 120 hours for the purpose of false malting.

Preferably, the oats are dormant, hulless oats.

Preferably, the increased avenanthramide concentration in the oats is greater than 750 ppm on a dry basis.

Preferably, the oats are de-hulled when the oats are covered and dormant oats.

Preferably, the oats are dried to a final moisture content of from about 3 to 10% dry basis.

Preferably, oats are anaerobically steeped to about 35% moisture content.

Preferably, an outer bran component and a residual de-branned groat are recovered using abrasion milling.

Preferably, the abraded bran component comprises from 3 to 30% of the initial weight of the oats prior to abrasion milling.

BRIEF DESCRIPTION OF THE DRAWINGS

These and other features of the invention will become more apparent from the following description in which reference is made to the appended drawings wherein:

FIG. 2 illustrates structures of the individual avenanthramides;

DETAILED DESCRIPTION OF PREFERRED EMBODIMENTS

Figure 1:
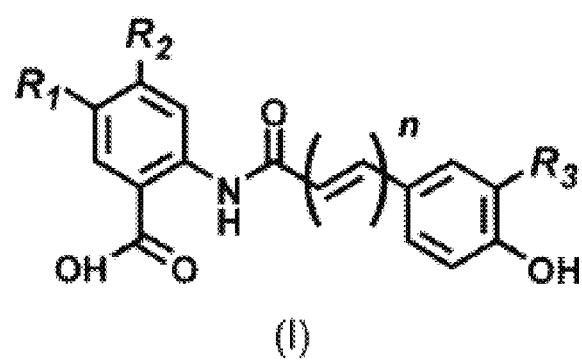
FIG. 1 shows a general structure formula of avenanthramides.

Reference will now be made in detail to some specific embodiments of the invention including the best modes contemplated by the inventors for carrying out the invention. Examples of these specific embodiments are illustrated in the accompanying drawings. While the invention is described in conjunction with these specific embodiments, it will be understood that it is not intended to limit the invention to the described embodiments. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well-known process operations have not been described in detail in order not to unnecessarily obscure the present invention.

In this specification and the appended claims, the singular forms "a," "an," and "the" include plural references unless the context clearly dictates otherwise. Unless defined otherwise, all technical and scientific terms used herein have the same meaning as commonly understood to one of ordinary skill in the art to which this invention belongs.

The present invention has been described with regard to one or more embodiments. However, it will be apparent to persons skilled in the art that a number of variations and modifications can be made without departing from the scope of the invention as defined in the claims.

The common oat (*Avena sativa*) is a species of cereal grain. Oats have a variety of uses. Oats for human consumption are used to make porridge, breakfast cereal, cookies and snack bars. In agriculture, one of the most common uses for oats is as livestock feed. Oats make up a large part of the diet for horses and are regularly fed to cattle as well. Oats are also used in some brands of dog and chicken feed. Oats have been cultivated for two thousand years in various regions throughout the world. Before being consumed as a food, oats were used for medicinal purposes, a use for which they are still honored. The growing of oats in Europe was widespread, and oats constituted an important commercial crop since they were a dietary staple for the people of many countries including Scotland, Great Britain, Germany and the Scandinavian countries.

The hulls, i.e. lemma and palea, play an important role during the development of kernels. The hulls supply the developing kernels with carbohydrates. Amino acids are the main source of nitrogen for the developing kernel, and a major portion of this may be contributed by the lemma and palea. In addition, being an outer cover, the lemma and palea may protect florets and kernels from attack by pathogens and insects.

Most oats, when harvested, have the hulls attached. There are also cultivars, for example, VAO-48, which are hulless, i.e. the hulls are loosely adhering to the kernel and are left in the field during combining and harvesting.

Mature oat kernels released from the mother plant in a dormant state can display either seed coat-imposed or embryo-based dormancy or both, known as primary dormancy.

The term "dormancy" is intended to describe a state in which seeds are temporarily prevented from germinating even under environmental conditions normally favorable for germination. These conditions may be a complex combination of water, light, temperature, gasses, mechanical restrictions, seed coats, and hormone structures. Seed dormancy has been described, for example, in "Genetic and Molecular Control of Seed Dormancy, B. Li and M. E. Foley, Trends in Plant Science, (1997) Vol. 2 (10), pp. 384-389, the contents of which are incorporated hereby by reference.

Dormancy delays germination and allows time for dispersal and prevents germination of all the seeds at same time. The staggering of germination safeguards some seeds and seedlings from suffering damage or death from short periods of bad weather or from transient herbivores.

Following a period of "after-ripening" and under environmentally favorable conditions, such as light, temperature, moisture, non-dormant kernels undergo a rapid transition resulting in the onset of germination.

However, partially or fully after-ripened non-dormant kernels exposed to unfavourable environmental conditions can exhibit an induced state of quiescence, known as "secondary dormancy".

The term "secondary dormancy" is intended to describe a state when some non-dormant and post-dormant seeds that are exposed to conditions that are not favorable for germination, such as high temperatures. The term "dormancy" is intended to include any seeds in a dormant state, including the primary dormancy, for example, but not limited to coat-imposed or true embryo dormancy; secondary dormancy, for example but not limited to, chemically induced, physically induced or any other form of induced dormancy, natural secondary dormancy; and any other forms of dormancy.

Many garden plants have seeds that will germinate readily as soon as they have water and are warm enough, though their wild ancestors had dormancy. These cultivated plants lack dormancy because of generations of selective pressure by plant breeders and gardeners that grew and kept plants that lacked dormancy.

Conversely, there are cultivars, for example, VAO-48 of the oat seeds described below, which have been genetically selected to have a prolonged secondary dormancy.

When oats are treated by soaking or steeping and allowed to germinate, as practiced during a typical malting process familiar to those skilled in the art of malting, the levels of avenanthramides increases in the sprouted seedlings, in a time-dependent manner, over initial avenanthramide levels in the dry seeds. The utility of a short period malting to enhance avenanthramide levels is limited by the modest increases in avenanthramides, and extended malting periods, for example, 4-5 days, results in a sprouted grain product with higher levels of avenanthramides but reduced utility in conventional milling and processing markets.

In accordance with one embodiment of the present invention, large quantities of avenanthramides are accumulated through the induction of secondary dormancy and false malting as described below. When oats in secondary dormancy are subject to a malting process, surprisingly, the avenanthramide levels can be dramatically increased by up to 25 to 35 fold, even though they do not germinate.

In other words, utilizing the secondary dormancy in a predictable manner to create conditions in which germination does not occur, may alter the nutritional value of whole kernels, as compared to sprouted grains.

During soaking and germination of dormant oats for up to 6 days, the avenanthramides continue to be produced, despite the fact that none of the macroscopic visual indicators of germination are observed, for example, radical emergence, branching and elongation, coleoptile and shoot expansion and elongation, etc. This treatment in which typical malting procedures are followed yet the grain in dormancy does not germinate are hereinafter referred to as "false malting".

The term "false malting" is intended to describe a treatment similar or identical to malting techniques as practiced by a person skilled in the art. However, as the seeds are in dormancy, for example in secondary dormancy, the seeds subjected to false malting do not germinate.

False malting represents a new technique for altering the composition of cereal grains in general, and oats in particular. Suppressing germination of oats during malting results in a whole oat product with elevated avenanthramide content conducive to incorporation into numerous established food, feed and industrial utilization markets.

Method of Quantitative Analysis of Avenanthramides

Determination of the qualitative and quantitative avenanthramide compositions of the oat material were performed as described below. Oat samples, i.e. seeds, were dried in an oven at 37° C. to constant weight (about 48 hours) and stored in vacuum pack plastic bags at −20° C. until analysis. Seeds were ground using a commercial coffee mill prior to extraction. Extractions and quantitative analyses were generally performed using two replicates.

Extraction

To 75 ml of refluxing acidified 80% ethanol (ethanol:water:glacial acetic acid, 80:19.9:0.1 (v/v/v)), 10 g ground oat sample was added with vigorous stirring along with 5 mg of sodium dithionite as antioxidant. The mixture was removed from the heat and allowed to cool for 20 minutes at room temperature with stirring. The entire content was then decanted into a graduated glass chromatography column equipped with a fritted disk. The suspension was left to settle by gravity forming a lightly-packed extraction bed (bed volume=$V_b$ mL) with a clear supernatant. The supernatant was collected by gravity flow, and the extraction bed eluted with $3 \times V_b$ of the acidified 80% ethanol by "percolation extraction" resulting in a clear greenish-yellow eluate.

Purification of Avenanthramides by Hydrophobic Interaction and Aromatic Absorption Chromatography:

To remove lipophilic components from this extract Octyl Sepharose™ CL 4-B chromatography beads were added (0.5 ml per g extracted), and the mixture concentrated to dryness in vacuuo at 40° C. by rotary evaporation. In order to prevent oxidation, distilled water was added to the mixture to ensure that the avenanthramide was precipitated during drying. The dried mixture was re-suspended in acidified 50% ethanol (ethanol:water:glacial acetic acid, 50:49.9:0.1 (v/v/v)) and quantitatively transferred to a graduated glass chromatography column containing Octyl Sepharose™ CL 4-B which had been previously gravity packed and pre-equilibrated in acidified 50% ethanol (e.g. for a 10 g sample, 25 ml, final bed volume $V_b$=30 mL). The column was then eluted with $3 \times V_b$ of the acidified 50% ethanol. The combined eluate was concentrated in vacuuo at 40° C. by rotary evaporation to give an essentially lipid-free extract.

To remove saponins, flavonoid glycosides, alcohol-soluble proteins and peptides, free sugars, aromatic, organic and amino acids, the concentrated extract was dissolved in a small volume (about 3 ml of acidified 40% ethanol (ethanol:water:glacial acetic acid, 40:59.9:0.1 (v/v/v)) per 10 g sample) and purified by chromatography using Sephadex™ LH-20. The solution was quantitatively transferred to a graduated glass chromatography column containing Sephadex™ LH-20, which had been previously gravity packed and pre-equilibrated in acidified 40% ethanol (e.g. for a 10 g sample, final bed volume $V_b$=25 ml). First, the saponins, free sugars, amino acids etc. were removed by eluting with $2 \times V_b$ of the acidified 40% ethanol. The absorbed avenanthramides were recovered by eluting with $3 \times V_b$ of acidified 95% ethanol (ethanol:water:glacial acetic acid, 95:4.9:0.1 (v/v/v)). Again, water was added before evaporation along with 5 mg of sodium dithionite to prevent oxidation. The eluate was concentrated to dryness in vacuuo at 40° C. by rotary evaporation to give the purified avenanthramide fraction.

HPLC Analysis of the Avenanthramide Fraction

In a first method, the purified avenanthramide fraction was dissolved in 5 ml 50% ethanol (ethanol:water, 50:50 (v/v)), filtered through a 0.45 µm filter and run on a HPLC. Samples (10 µl) were injected using a Rheodyne™ injector into a $C_{18}$ reversed-phase column (ODS Hypersil™ $C_{18}$, 5 µm, 4.6 mm×250 mm) maintained at 25° C. using a CERA Column Cooler 250 equipped with a $C_{18}$ guard column. HPLC analyses were performed using a Thermo Separation Products (TSP) Spectra System P4000 pump and monitored at 330 nm using a TSP SpectraSystem™ UV3000 spectral scan detector and ChromQuest software. The flow rate was maintained at 0.8 ml per min. Solvents for HPLC were A: methanol, B: water and C: 5% acetic acid. The solvent gradient (vol. %) consisted of 40A:55B:5C, linearly increasing to 50A:45B:5C over 40 min, and linearly increasing to 80A:15B:5C over 15 min, then reaching 100A over 3 min and holding for 3 min. The solvent gradient was brought back to original conditions over 3 min, allowed equilibrating for 4 min. All major avenanthramide peaks were identified by comparison of relative retention time and UV spectra (monitored from 240 to 380 nm) with authentic standards. All minor avenanthramides were identified by HPLC-mass-spectrometry alone.

In a second method, the solvent system of the first method was changed as follows: Solvents for HPLC were A: methanol, B: water and C: 0.1 M phosphoric acid. The solvent gradient (vol. %) consisted of 45A:45B:10C, linearly increasing to 60A:30B:10C over 55 min, then reaching 100A over 3 min and holding for 3 min. The solvent gradient was brought back to original conditions over 3 min, allowed equilibrating for 4 min.

In a third method, samples (10 µl) were injected into a $C_{18}$ reversed-phase column (Zorbax Stable™ bond $C_{18}$, 3.5 µm, 4.6 mm×150 mm) maintained at 30° C. Solvents for HPLC were A: methanol, B: water and C: 0.5M formic acid. The solvent gradient (vol. %) consisted of 45A:45B:10C, linearly increasing to 55A:35B:10C over 24 min, and linearly increasing to 70A:20B:10C over 9 min, then reaching 95A:5C over 3 min and holding for 3 min. The solvent gradient was brought back to original conditions over 3 min, allowed equilibrating for 3 min.

HPLC Mass Spectrometric Analysis of the Avenanthramide Fraction

Minor avenanthramide peaks were identified by HPLC-MS-MS using a Thermo Finnigan LCQ Advantage™ mass spectrometer equipped with a Surveyor™ HPLC-UV diode-array detector system (HPLC conditions: Hypersil™ ODS, 120 Å, 5µ, 250×4.6 mm column. HPLC UV monitoring was performed at 330 nm. The same solvent system was used as described above in the first method at a flow rate of 0.8 mL per min. The solvent gradient (vol. %) consisted of 40A:55B:5C, linearly increasing to 60A:35B:5C over 80 min, and linearly increasing to 80A:15B:5A over 5 min, then reaching 100A over 3 min and holding for 3 min. The solvent gradient was brought back to original conditions over 3 min, allowed equilibrating for 3 min. MS-MS conditions: electro-spray ionization (ESI, negative mode), source voltage: 4.5 Kvolts, capillary voltage: −10 volts, capillary temp: 300° C., sheath gas flow: 80% full, auxiliary gas flow: 20% max (No stream splitting).

Quantitative Estimation of Avenanthramides

Individual avenanthramides were quantified by determining the peak areas at 330 nm relative to an external authentic avenanthramide A standard and expressed as avenanthramide A weight equivalents. Total avenanthramides were calculated by summing all the individual avenanthramide quantities calculated as avenanthramide A weight equivalents and expressed as parts per million (ppm) avenanthramide A equivalents on a dry weight basis.

Avenanthramides are a group of about 30 different N-aroylanthranilic acid alkaloids of the general formula depicted in FIG. 1. FIG. 2 illustrates structures of the individual avenanthramides occurring in both malted and un-malted oats.

Figure 3:
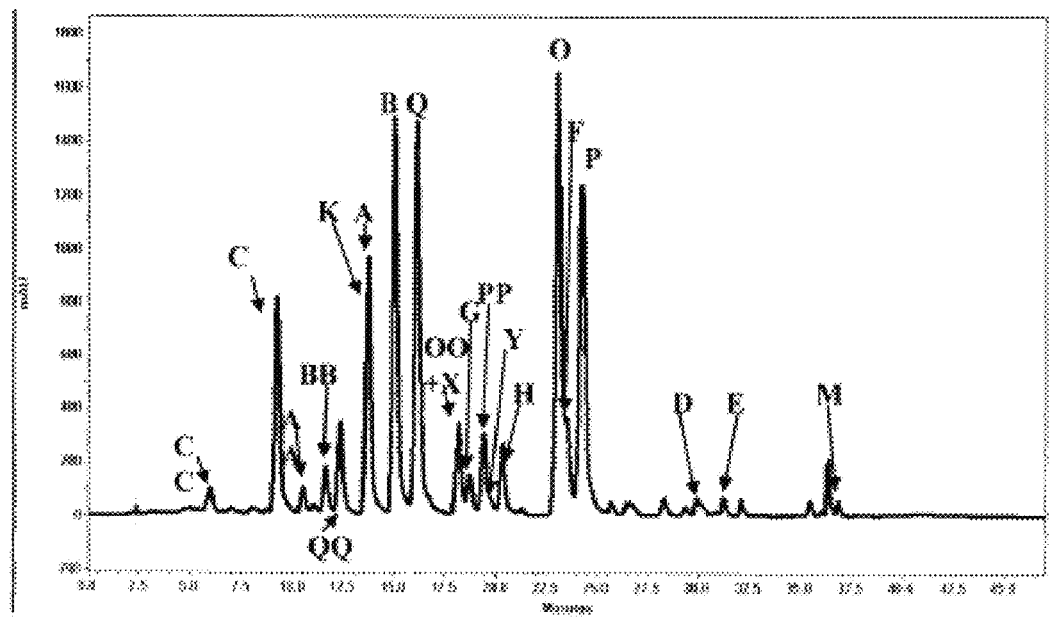
FIG. 3 illustrates a typical HPLC profile of the avenanthramide fractions.

FIG. 3 illustrates a typical HPLC profile of the avenanthramide fractions from oats using the third method as described above malted and with the assigned nomenclature in FIG. 2.

Figure 4:
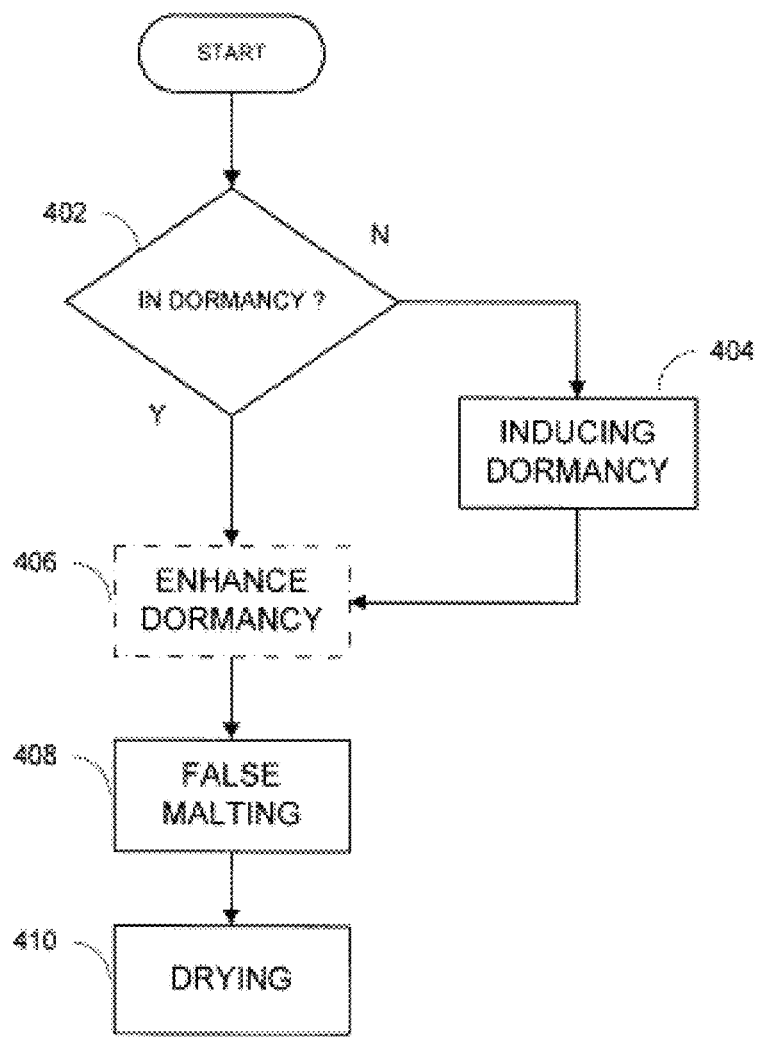
FIG. 4 shows steps of an exemplary method for increasing the concentration of avenanthramides.

FIG. 4 shows steps of a method for increasing the concentration of avenanthramides in accordance with an embodiment of the present invention.

If the oats are not in dormancy 402, a secondary dormancy may be induced 404. Otherwise the oats are in dormancy, generally in natural or induced secondary dormancy.

Seeds in secondary dormancy may lose the dormancy over time, therefore, even if the seeds are in dormancy, an optional step may be included to enhance the dormancy 406.

One non-limiting method to induce or enhance the secondary dormancy is to anaerobically hydrate, or tempering, the oats.

Malting generally starts with steeping of oats in water until oats reach a certain moisture content. The steeping is generally interspersed with airing the oats, allowing the oats to get additional oxygen.

The dormancy of oats may be induced 404 or enhanced 406 through anaerobically steeping. With anaerobically steeping, the oats are tempered or hydrated anaerobically, for example, at temperatures greater than 30° C. for 12 to 18 hours.

The oats are then subjected to false malting 408, i.e. at a condition similar or identical to malting, but without germination, for example at 23-37° C. for 96 to 120 hours. Following the false malting, the oats are dried 410, for example, at 35° C. for 24 to 48 hours, before storage or further processing.

Following are non-limiting examples showing the increase of concentration of avenanthramides in accordance with the embodiments of the present invention.

Example 1: Dormant Vs. Non-Dormant Oats

Seed samples of a freshly harvested dormant, hulless, bald seeded oat breeding line (VAO-48) and those of a non-dormant, hulless, bald seeded oat breeding line (VAO-2, now registered as variety AC GEHL) were malted as described below.

Approximately 20 g of each breeding line were briefly surface sterilized by immersion in aqueous 1% sodium hypochlorite solution for 20 min at room temperature with gentle agitation then removed and thoroughly rinsed to eliminate excess sodium hypochlorite solution. The seeds were then germinated in covered Petri dishes (150×15 mm) on moist filter paper disks at room temperature and diffuse light for 4 days. A separate sample of 20 g of each breeding line was set aside as a control.

After four days the germination rates of the two samples were determined. The seeds, including both germinated and non-germinated, were then removed and dried in a seed dryer at room temperature for two days. The average germination rates were:

Dormant, hulless, bald (VAO-48) . . . 1%
Non-dormant, hulless, bald (VAO-22) . . . 75%

The total avenanthramide contents of the two samples both before and after (false) malting were determined using the first method described above and are summarized in Table 1:

TABLE 1

Avenanthramide accumulation in dormant and non-dormant oats

| Oat type | Material | Total avenanthramides | % increase | Fold increase |
|---|---|---|---|---|
| Dormant | Before malting | 77 ppm | | |
| | After false malting | 534 ppm | 590 | 6.9 |
| Non-dormant | Before malting | 54 ppm | | |
| | After malting | 340 ppm | 530 | 6.3 |

Table 1 shows that, the dormant oats surprisingly accumulated avenanthramides during the false malting period.

The dormant seeds have similar morphology as the starting material, and unlike the non-dormant seeds, were free of roots, coleoptiles and emerging leaves and shoots.

Example 2: Effect of Anaerobic Steeping and Storage of Dormant Seed on Dormancy

It is known that dormant oats lose their secondary dormancy with time, depending on the conditions of storage (e.g. oxygen level, temperature, moisture content). In particular, low oxygen levels prolong dormancy and/or inhibit germination. It is also known to oat breeders and persons skilled in the seed germ plasma preservation art that seeds stored at sub-zero temperatures (e.g. −20° C.) can retain most of their genetically-inherited traits for long periods of time. However, to be practical for a large-scale process such as malting, a constant supply of dormant oats should be available on a regular basis throughout the year, without reliance of costly cold temperature storage to maintain the seed dormant. It is therefore preferable to prolong and to enhance dormancy in dormant oats, and to induce a secondary dormancy in non-dormant oats.

Seeds of the dormant oat line used in Example 1 (VAO-48), that had been stored for 3 weeks at room temperature, then 1 week at −20° C., were submersed for various times up to about 48 hours in tap water, at approximately 23° C. In a small scale experiment, seeds were distributed into airtight Petri dishes completely filled with water and sealed with Parafilm (i.e. anaerobic steeping). After approximately 2, 4, 6, 8, 12, 24, and 48 hours, the seeds were removed and briefly air dried in a seed dryer at room temperature. The seeds were then surface sterilized and malted as above for four days at room temperature in diffuse light. After four days, the rate of germination was determined as above.

In a further experiment larger quantities of seed were used and the anaerobic steeping was carried out in an airtight Erlenmeyer flask filled with tap water and sealed with Parafilm™. This "tapering" at the top of the flask configuration facilitated the exclusion of residual air and assured submersion of the seeds below the water level. The results of both experiments are summarized in Table 2.

TABLE 2

Effect of anaerobic steeping time on germination

| Steeping duration | Petri dish % germination after four days | Erlenmeyer Batch % germination after four days |
|---|---|---|
| 0.0 hours | 48.5 ± 4.5 | 35.5 ± 3.5 |
| 2.0 hours | 30.0 ± 1.0 | 22.0 ± 1.0 |
| 4.0 hours | 16.5 ± 2.5 | 10.5 ± 5.5 |
| 6.0 hours | ND | 9.5 ± 6.5 |
| 8.0 hours | 6.0 ± 2.0 | 2.5 ± 0.5 |
| 11.75 hours | 3.0 ± 1.0 | ND |
| 24.0 hours | 19.5 ± 9.5 | ND |
| 47.5 hours | 16.5 ± 1.5 | ND |

It was found that, by simply soaking or steeping the seeds over night, approximately 8 to 18 hours, without exposure to air, the germination rate dropped considerably, from about 50% with no steeping to less than 10% after anaerobic steeping. This indicates that germination can be substantially decreased by anaerobic steeping for 8 to 18 hours. Further experiments to optimize the steeping temperature indicated a temperature of 30° to 32° C. for 18 hours resulted in a consistent germination rate of less than 3% germination (i.e. >97% dormancy).

To test the retention of the dormancy attributes of the dormant oat line after various storage periods, germination experiments were performed using samples stored at room temperature for various time periods up to 14 weeks. In addition, duplicate samples were additionally subjected to anaerobic steeping over night, briefly air dried, and then tested for germination under similar conditions. In both time course experiments seed were germinated in Petri dishes at room temperature and diffuse light for four days and the germination rates calculated. The results of both experiments are shown in Table 3.

TABLE 3

Effect of storage and anaerobic steeping on germination

| Weeks stored at 23° C. | No steeping % germination | Anaerobic steeping at 32° C. % germination |
|---|---|---|
| 0 | 35.0 ± 2.6 | 6.7 ± 2.1 |
| 2 | 1.0 ± 1.0 | 2.3 ± 2.3 |
| 4 | 2.7 ± 0.6 | 3.7 ± 0.6 |
| 6 | ND | ND |
| 8 | 9.0 ± 2.0 | 2.0 ± 1.0 |
| 10 | 29.0 ± 3.6 | 7.0 ± 3.6 |
| 14 | 89.7 ± 1.5 | 30.3 ± 4.0 |

The dormancy of the dormant oat line increases during the first 8 to 10 weeks of storage then decreases dramatically such that about 90% of the seeds germinate. As expected the oats anaerobically steeped for 16 hours showed greater dormancy after storage of 8 weeks or more at room temperature than the corresponding non-steeped samples. In this way, the dormancy of the oats which gradually lose dormancy on storage at room temperature can be enhanced and thus more suitable for this process.

Example 3: Effects of Heat Pre-Treatment and Anaerobic Steeping on Dormancy and Avenanthramide Accumulation in Non-Dormant, Hulless Oats There are other methods to enhance and to induce a secondary dormancy. A non-limiting exemplary method of enhancing and inducing the dormancy of oats is to treat the oats with dry heat at from 30 to 70° C. for various periods of time up to 2 weeks. This procedure is usually carried out in 2 phases: The first phase involves temperatures of about 30° C. for several days to bring the moisture content of the seed down to about 3% followed by a $2^{nd}$ phase at about 70° C. for up to a week. Such a treatment has also been shown to be effective in reducing seed-born mould and bacterial spores. Under this regime the seeds are not damaged and in some cases, the germination rate is in fact increased.

Seeds (500 g) of the non-dormant hulless oat line (VAO-2) were heat treated in a convection drying oven at 37° C. for 72 hours and then 70° C. for 144 hours. After cooling to room temperature, the heat-treated seed was divided into sub-samples, one group (5 replicates) anaerobically steeped for 18 hours at 32° C., the other group not anaerobically steeped (5 replicates). Both groups were surface sterilized as above, then malted in Petri dishes (150×50 mm) in diffuse light at room temperature for four days. After malting, the seeds were evaluated for rate of germination (% germinated) and avenanthramide content using the first method described above (μg avenanthramide A equivalents/g dry wt=ppm avenanthramide A). The results are summarized in Table 4.

TABLE 4

Effects of anaerobic steeping on germination rate and avenanthramide accumulation in heat pre-treated, non-dormant oats after four days malting

| Treatment | % germinated (±SD) | Avenanthramide content, (Avenanthramide A equivalents) | | | |
|---|---|---|---|---|---|
| | | Avenanth A (ppm) | Avenanth B (ppm) | Avenanth C (ppm) | Total Avenanth (ppm) |
| Not heated, not steeped | 35.0 ± 2.6 | ND | ND | ND | 77 |
| Heated, but not steeped | 14.9 ± 4.2 | 34.2 | 42.7 | 24.9 | 272.4 |
| Heated and steeped | 0.4 ± 0. | 42.3 | 64.0 | 40.7 | 445.1 |

As described above, both dry heating of the oats under the two-phase heating treatment, and anaerobic steeping for 18 hours separately reduced the germination of the oats during malting (i.e. dormancy increased). When used in concert, heat treatment followed by anaerobic steeping, the germination rate was lowered to virtually 0% and the seeds remained dormant throughout the four day malting period. Furthermore, the total avenanthramide content of the four day "false malted" oats from the combined heat and anaerobic steeping treatments rose from 77 ppm at the start, to 445 ppm after malting, representing an increase of about 480% (5.8-fold) over initial values.

It is noted that the two-phase dry heating process for inducing dormancy did not result in loss of viability. When the heat treated oats were incubated in the presence of 100 ppm gibberellin (e.g. $GA_3$) for 5 days, almost complete restoration of germination was observed.

Example 4: Effects of Temperature on Avenanthramide Accumulation During False Malting In traditional malting, optimum temperatures are chosen to maximize germination and the concurrent hydrolysis of starch reserves of the seed to free sugars for subsequent fermentation. For these purposes optimal temperatures are usually below about 25° C. To study the effect of temperature on the accumulation of avenanthramides a false malting was carried out at four different temperatures in the dark for four days. For comparison, a false malting was also done in diffuse light at room temperature. For these studies, a non-dormant, hulless oat variety that had been rendered dormant by heat pretreatment and anaerobic steeping was used.

The four temperatures for the process were 3° C., 23° C. (room temperature), 30° C., and 37° C. and the false malting was carried out in the dark with a comparison sample malted at 23° C. in diffuse light. The malting at 3° C. was carried out in a laboratory refrigerator, and the malting at 30° C. and 37° C. were carried out in a controlled temperature convection oven.

Using 50 g sample of AC Baton hulless oats (AC Baton, rate of germination>95%). The seeds were heat treated as follows: 72 hours at 37° C. followed by 144 hours at 70° C. as in Example 3 above, briefly cooled to room temperature (23° C.) then anaerobically steeped in tap water at 32° C. for 18 hours and air dried in a seed dryer for about four hours. The seeds were surface sterilized as above only using 0.25% aqueous sodium hypochlorite solution at room temperature for 1 hour, then divided into four sub-samples and 'false malted" at the four different temperatures in the dark for 96 hours, using the controlled temperature convection oven of Example 3.

After malting, the seeds were evaluated for rate of germination (% germinated), air dried in a seed dryer at room temperature overnight, and the avenanthramide content determined by the first method described above (μg avenanthramide A equivalents/g dry wt=ppm avenanthramide A). The content of the three major avenanthramides (avenanthramides A, B, and C), all other avenanthramides, and the total avenanthramides were calculated and compared with corresponding levels in unmalted material. The results are summarized in Table 5:

TABLE 5

Effects of temperature during a four day false malting of
a non-dormant oat (AC Baton) on avenanthramide accumulation

| | | avenanthramide content, (avenanthramide A equivalents) | | | | |
|---|---|---|---|---|---|---|
| Treatment | % germ. (±SD) | Avenanth. A (ppm ± SD) | Avenanth. B (ppm ± SD) | Avenanth. C (ppm ± SD) | All others (ppm ± SD) | Total Avenanth (ppm ± SD) |
| Control | 96.0 ± 2* | (28.0 ± 0.6)* | (29.4 ± 0.3)* | (16.1 ± 4.5)* | (40.6 ± 3.1)* | (114.1 ± 8.5)* |
| 4 days at 3° C. in dark | 0.0 ± 0.0 | 31.1 ± 0.2 | 38.2 ± 0.2 | 22.4 ± 0.5 | 50.6 ± 3.2 | 142.2 ± 4.1 |
| 4 days at 23° C. in dark | 3.1 ± 1.3 | 71.4 ± 4.7 | 88.0 ± 7.7 | 65.3 ± 4.7 | 390.9 ± 21.6 | 615.6 ± 38.7 |
| 4 days at 30° C. in dark | ND | 106.3 ± 0.7 | 178.1 ± 1.9 | 150.2 ± 6.5 | 751.7 ± 42.7 | 1,186.3 ± 51.7 |
| 4 days at 37° C. in dark | 0.0 ± 0.0 | 276.4 | 251.6 | 234.3 | 1,235.3 | 1,997.6 |

*Values for % germination represent four day germination rate. Values for avenanthramides in brackets represent pre-malting levels.

From a comparative standpoint, Table 5 shows that the levels of accumulated avenanthramides A, B, C, and all other avenanthramides increased during false malting with increasing malting temperature. The lowest temperature used (3° C.) produced an increase from 114 ppm in the un-malted material to about 142 ppm after malting (about 25% or 1.25 fold) while the highest temperature (37° C.) resulted in total avenanthramide levels of almost 2,000 ppm (about 1,650% or 17.5 fold). Under the pretreatment regime used here, both high and low temperatures decreased germination slightly.

Figure 5:
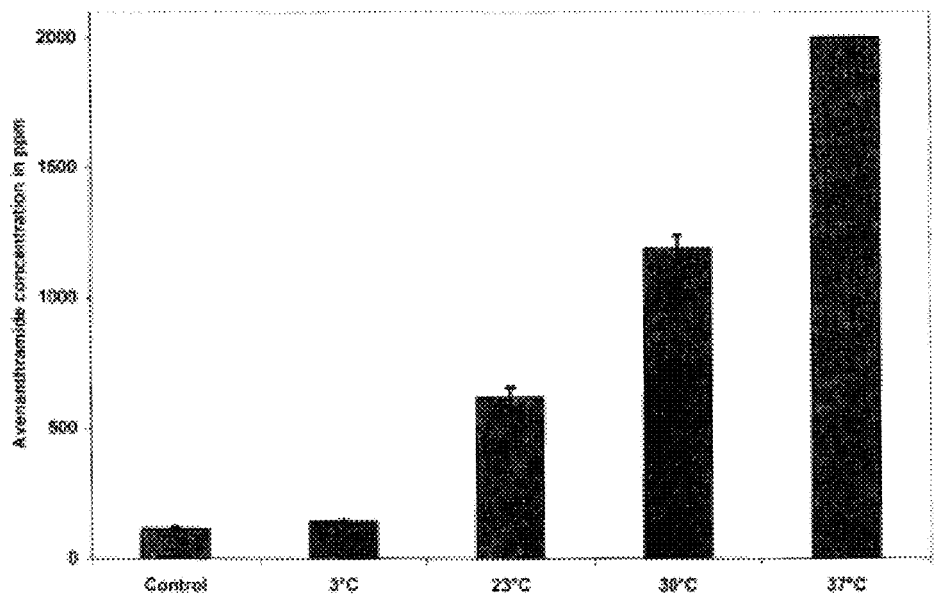
FIG. 5 shows effect of temperature on total avenanthramide concentration of heat treated, anaerobically steeped, hulless oats.

The effect of temperature on the total avenanthramides accumulated during 96 hours false malting using a non-dormant (>95% viable seed) hulless oat AC Baton which was made dormant by the heating and anaerobic steeping procedure is shown in FIG. 5. The dramatic increases over control (i.e. un-malted) seeds exhibited by simply malting at temperatures above those used in most practiced malting art (usually 10 to 25° C.) can be readily seen.

Example 5: Effects of Time on Avenanthramide Accumulation During False Malting

To study the time course of avenanthramide accumulation during the false malting process, the process was carried out for various periods using a non-dormant hulless oat variety, and the levels of avenanthramides accumulated were determined.

Using 120 g sample of AC Baton hulless oats (AC Baton, rate of germination>95%). The seeds were heat treated as in Example 3, briefly cooled to room temperature (23° C.) then anaerobically steeped in tap water at 32° C. for 18 hours and air dried in a seed dryer for about four hours. The seeds were surface sterilized as in Example 4, then 'false malted" in the dark at 37° C. for various time periods in a shallow tray on moist paper towels and covered with aluminum foil. The germination rate was less than 1% after four days. After each malting period, a representative sub-sample (approximately 30 g) of the seeds was removed, dried at room temperature (forced air) for four hours then brought to constant weight by drying at 37° C. for ~40 hours and stored at −20° C. until analyzed for avenanthramide content by HPLC using the first method described above (µg avenanthramide A equivalents/g dry wt=ppm avenanthramide A), and compared to un-malted material. The results are summarized in Table 6 and shown in FIG. 6

TABLE 6

Time course of avenanthramide accumulation during "false malting"
of non-dormant AC Baton oats at 37° C.

| | Avenanthramide content, (Avenanthramide A equivalents) | | | | |
|---|---|---|---|---|---|
| Time (hrs) | Avenanth A (ppm ± SD) | Avenanth B (ppm ± SD) | Avenanth C (ppm ± SD) | All others (ppm ± SD) | Total Avenanth (ppm ± SD) |
| Control (0) | (28.0 ± 0.6)* | (29.4 ± 0.3)* | (16.1 ± 4.5)* | (40.6 ± 3.1)* | (114.1 ± 8.5)* |
| 24 | 75.3 ± 0.4 | 62.0 ± 0.8 | 55.9 ± 1.8 | 126.6 ± 0.6 | 319.8 ± 2.3 |
| 48 | 111.8 ± 0.3 | 104.3 ± 0.9 | 76.8 ± 1.9 | 291.3 ± 2.6 | 584.2 ± 5.7 |
| 72 | 139.1 ± 1.0 | 148.9 ± 0.8 | 88.6 ± 3.2 | 461.5 ± 0.1 | 838.1 ± 3.2 |
| 96 | 144.4 ± 17.9 | 175.6 ± 28.4 | 79.9 ± 17.9 | 557.3 ± 92.8 | 957.2 ± 161.3 |

*Values for avenanthramides in brackets represent pre-malting levels.

Figure 6:
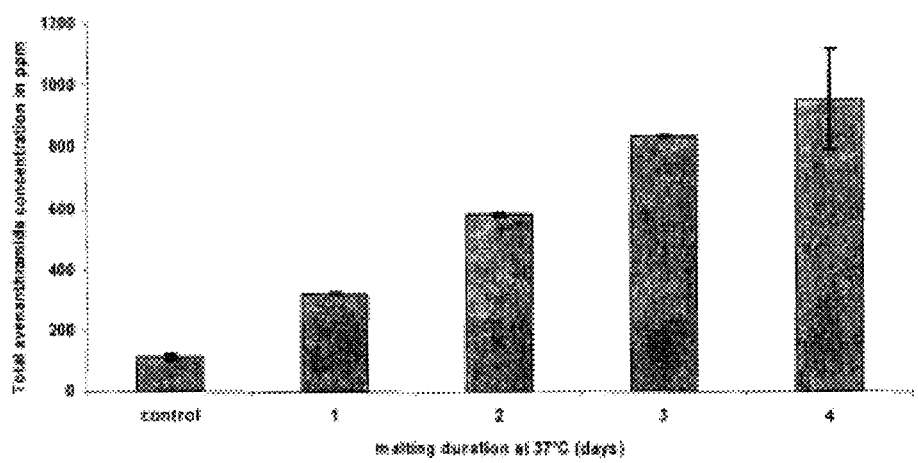
FIG. 6 shows time course of avenanthramide accumulation in non-dormant oats during false malting at 37° C.

From the data in Table 6 and FIG. 6, it can be seen that the level of avenanthramides A, B, C and total avenanthramides all increased with time during the false malting period, and the time course of the increase follow a somewhat linear pattern up to day 3 and leveling off by day 4. The overall four day accumulation of total avenanthramides represented an approximately 740% (8.4 fold) increase over the initial value.

Example 6: Effects of Calcium Ion Steeping Treatment on Avenanthramide Accumulation During False Malting of Dormant Oat VAO-48

To examine if the presence of $Ca^{+2}$ ion during the anaerobic steeping phase has any effect on the accumulation of avenanthramides during the subsequent malting phase, a series of increasing $Ca^{+2}$ concentrations were used in the steep water and the avenanthramide content determined after malting.

25 g samples of the hulless, hairless, dormant oat VAO-48 was anaerobically steeped in either water or various concentrations of USP-grade $CaCl_2.(H_2O)_2$ solutions at 35° C. After steeping for 18 hours and air drying in a seed dryer for about four hours, the seeds were surface sterilized as above then 'false malted" using Petri dishes (150×50 mm) in the dark at 30° C. in a controlled temperature oven for four days. The germination rate in all cases was less than 1% after four days. After malting the seeds were removed, dried at room temperature (forced air) for four hours then brought to constant weight by drying at 37° C. for ~40 hours and stored at −20° C. until analyzed for avenanthramide content by the third method described above (μg avenanthramide A equivalents/g dry wt=ppm avenanthramide A), and compared to un-malted material. The results are summarized in Table 7.

As shown in the Table 7 the level of individual avenanthramides was very low in the unmalted seeds and the total avenanthramide content prior to malting was only about 32 ppm. After steeping in water without added calcium ion, and a four day malting at 30° C. the levels of all avenanthramides were much higher and the total avenanthramide concentration of 439 ppm represented an approximately 13.7 fold increase. With increasing $Ca^{+2}$ concentration in the steep water, the avenanthramide concentration in the malted grains showed an increasing trend, with an increase over steeping with no added $Ca^{+2}$ of from about 439 ppm to about 757 ppm at 1% added $Ca^{+2}$ (approximately 1.7 fold) and an overall increase over un-malted seeds at 1% $Ca^{+2}$ of about 23.6 fold. These results show that the addition of $Ca^{+2}$ during the steeping period enhances the subsequent accumulation of avenanthramides during malting.

Example 7: Effects of High Concentrations of Calcium Chloride Steeping Treatment on Avenanthramide Accumulation During False Malting of Non-Dormant Oat VAO-22

Non-dormant, hulless, hairless oat line VAO-22 and a higher concentration of $Ca^{+2}$ in the steep water was used in Example 7.

A 1,300 g sample of VAO-22 hulless, hairless, non-dormant oat breeder's seed was used (84% germination rate after four days). The seeds were then heat treated as in Example 5. A 25 g sample was used as a control representing the un-malted seeds and stored at −20° C. until analyzed. The rest of the heat treated material was anaerobically steeped at 35° C. in either 1.0% or 2.0% $Ca\ Cl_2.(H_2O)_2$ for 18 hours and air drying in a seed dryer for about four hours. The seeds were then surface sterilized as above and 'false malted" in the dark at 30° C. in a controlled temperature oven for four days using Petri dishes (150×50 mm). After malting the seeds were removed, dried at room temperature (forced air) for four hours then brought to constant weight by drying at 37° C. for ~40 hours and stored at −20° C. until analyzed for avenanthramide content by HPLC using the third method described above (μg avenanthramide A equivalents/g dry wt=ppm avenanthramide A), and compared to un-malted material. The results are summarized in Table 8.

As can be seen in Table 8, the individual and total avenanthramide levels of this variety of oats increased during a four day false malting after steeping in $CaCl_2$ at concentrations of both 1 and 2%. For example avenanthramide B increased from 3.4 ppm to almost 80 ppm (2,240%; 23.4 fold over initial value) when anaerobically steeped for 18 hrs in 1% $CaCl_2$ and false malted for four days at 30° C. while at 2% $CaCl_2$, the level reached 103 ppm (2,930%; 30.3 fold over initial). For avenanthramide C, the corresponding increases were from 2.3 ppm to 65.2 ppm (2,735%; 28.4 fold over initial) at 1% $CaCl_2$ and to 100.1 ppm (4,252%; 43.5 fold over initial) at 2% $CaCl_2$. Other avenanthramides similarly increased and the total avenanthramide levels represented levels of 2,307% and 3,190% at 1% and 2% $CaCl_2$ (24.1 and 31.9 fold over initial) respectively. The data in these two examples clearly support an enhancing role of $CaCl_2$ at a concentration range of at least up to 2% added during the anaerobic steeping step, on the subsequent accumulation and/or retention of avenanthramides in the malted oats.

TABLE 7

Effects of $CaCl_2$ concentration during anaerobic steeping on the accumulation of avenanthramides during false malting of VAO-48 at 30° C.

| $CaCl_2$ concentration added to steeping water | Avenanthramide content, (Avenanthramide A equivalents) | | | | |
| --- | --- | --- | --- | --- | --- |
| | Avenanth A (ppm ± SD) | Avenanth B (ppm ± SD) | Avenanth C (ppm ± SD) | All others (ppm ± SD) | Total Avenanth (ppm ± SD) |
| Un-malted | 5.21 ± 0.10 | 6.30 ± 0.35 | 2.72 ± 0.28 | 17.88 ± 2.08 | 32.12 ± 2.82 |
| 0% | 32.4 ± 1.8 | 103.9 ± 7.4 | 63.5 ± 8.9 | 239.2 ± 26.4 | 438.9 ± 44.5 |
| 0.05% | 37.7 ± 5.6 | 122.0 ± 14.8 | 81.5 ± 9.4 | 287.3 ± 30.9 | 528.4 ± 30.9 |
| 0.10% | 27.2 ± 11.4 | 113.4 ± 5.8 | 75.7 ± 4.6 | 251.4 ± 10.4 | 467.7 ± 32.1 |
| 0.50% | 59.9 ± 1.1 | 155.3 ± 2.3 | 126.4 ± 2.8 | 400.1 ± 0.3 | 741.7 ± 6.5 |
| 1.0% | 68.7 ± 3.3 | 149.0 ± 8.2 | 138.1 ± 4.0 | 401.1 ± 15.4 | 757.0 ± 30.9 |

TABLE 8

Effects of CaCl$_2$ concentration during anaerobic steeping on the accumulation of avenanthramides during false malting of VAO-22 at 30° C.

| CaCl$_2$ concentration added to steeping water | Avenanthramide content, (Avenanthramide A equivalents) | | | | |
|---|---|---|---|---|---|
| | Avenanth A (ppm ± SD) | Avenanth B (ppm ± SD) | Avenanth C (ppm ± SD) | All others (ppm ± SD) | Total Avenanth (ppm ± SD) |
| Un-malted | 2.6 ± 0.37 | 3.4 ± 0.77 | 2.3 ± 0.39 | 13.7 ± 1.5 | 22.1 ± 3.01 |
| 1.0% | 27.0 ± 0.22 | 79.7 ± 0.26 | 65.2 ± 0.26 | 360.1 ± 2.4 | 532.0 ± 3.16 |
| 2.0% | 46.7 ± 0.08 | 103.0 ± 0.06 | 100.1 ± 0.38 | 461.7 ± 8.8 | 711.4 ± 9.32 |

Example 8: Effects of Satake Milling of Dormant Oat VAO 48 Oats Before and after False Malting, on the Accumulation of Avenanthramides in the Bran and De-Branned Groat Dry Milled Fractions As previously noted the false malting gives rise to an oat kernel that is for the most part essentially the same as an un-malted kernel and therefore readily usable for processing into a bran and a de-branned product through conventional dry abrasion milling, for example, Satake milling.

A sample (~380 g) of the hulless, hairless, dormant oat VAO-48 was milled using a Satake to give the following sequential fractions:

0-7% (by weight) bran fraction
7-15% (by weight) bran fraction
15-23% (by weight) bran fraction
>23% (by weight) de-branned groat All mill fractions were immediately chilled on ice and stored at −20° C. until analyzed.

Figure 7:
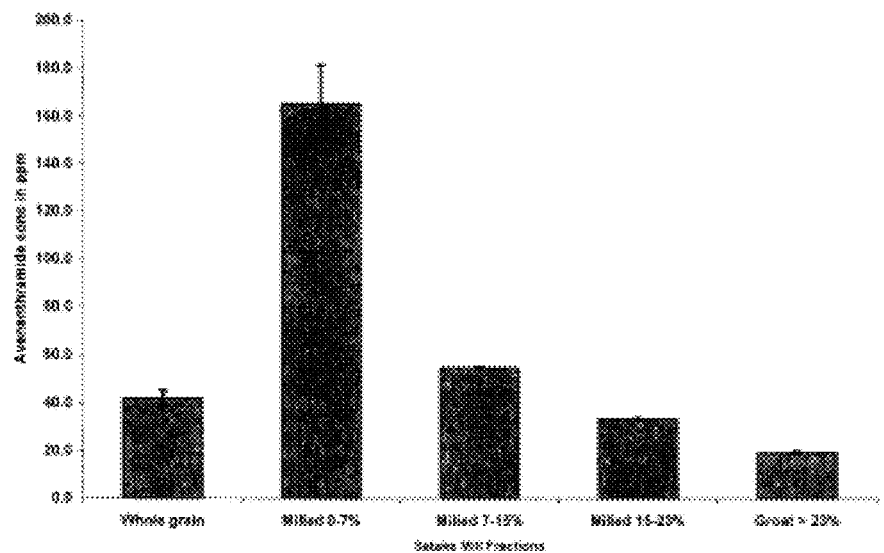
FIG. 7 illustrates distribution of total avenanthramide in un-malted kernel as determined by Satake dry milling.

Duplicate samples of the un-milled whole seed and the Satake mill fractions were analyzed for avenanthramide content by HPLC using the first method described above (µg avenanthramide A equivalents/g dry wt=ppm avenanthramide A) and the results are summarized in Table 9 and FIG. 7.

Figure 8:
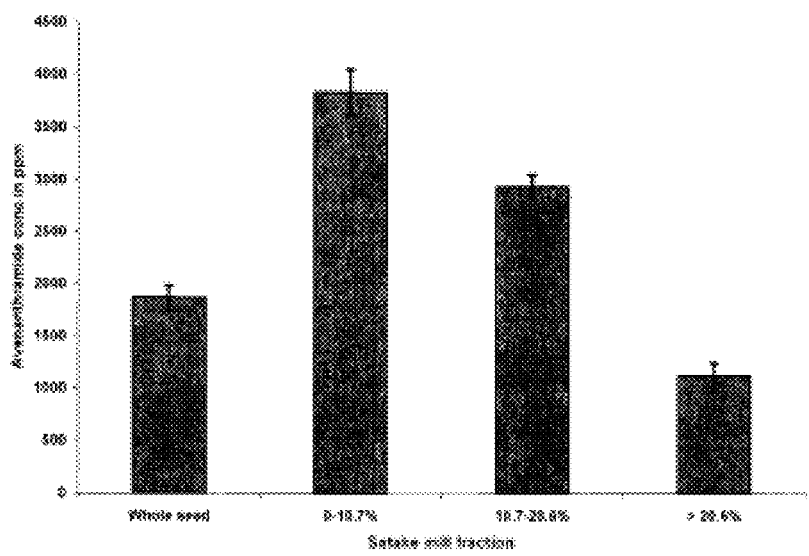
FIG. 8 illustrates distribution of total avenanthramide in kernel in one cultivar (VAO-48) after false malting as determined by Satake dry milling.

A further sample (377 g) of the same material, which had been heat treated as above in Example 5 and stored at −20° C. until used, was anaerobically steeped in tap water at 35° C. for 18 hours. The seeds were surface sterilized as in Example 4, then 'false malted" at 30° C. in a controlled temperature oven for four days. The germination rate in all cases was less than 1% after four days. After malting the seeds were removed, dried to constant weight at 37° C. in a controlled temperature oven and stored at −20° C. until milled. The following Satake mill fractions were prepared as above:

0-10.7% (by weight) bran fraction
10.7-20.6% (by weight) bran fraction
>20.6% (by weight) de-branned groat Duplicate samples of the un-milled whole malted oats and each of the mill fractions were analyzed for avenanthramide content by HPLC using the second method described above (µg avenanthramide A equivalents/g dry wt=ppm Avenanth. A). The results are summarized in Table 10 and FIG. 8.

TABLE 9

Levels of avenanthramides in whole seeds and Satake abrasion milling fractions of un-malted VAO-48 oats

| Un-malted material used | Avenanthramide content, (Avenanthramide A equivalents) | | | | |
|---|---|---|---|---|---|
| | Avenanth A (ppm ± SD) | Avenanth B (ppm ± SD) | Avenanth C (ppm ± SD) | All others (ppm ± SD) | Total Avenanth (ppm ± SD) |
| Whole seed | 8.5 ± 0.7 | 9.9 ± 1.1 | 2.3 ± 0.6 | 21.1 ± 1.0 | 41.9 ± 3.4 |
| 0-7% bran fraction | 23.0 ± 0.2 | 25.3 ± 1.5 | 7.0 ± 2.2 | 110.0 ± 12.1 | 165.3 ± 16.0 |
| 7-15% bran fraction | 10.5 ± 0.7 | 13.5 ± 0.7 | 7.3 ± 0.3 | 23.6 ± 1.9 | 54.9 ± 0.2 |
| 15-23% bran fraction | 7.1 ± 0.5 | 9.1 ± 0.6 | 2.0 ± 0.1 | 15.2 ± 0.7 | 33.4 ± 0.3 |
| >23% de-branned groat | 4.4 ± 0.2 | 5.2 ± 0.5 | 1.3 ± 0.1 | 8.3 ± 0.2 | 19.2 ± 0.5 |

As shown in Table 9, the avenanthramide content of un-malted VAO-48 oats varied considerably between fractions, with the highest levels (almost four times the level in whole kernels) exhibited by the outermost (i.e. 0-7%) bran layer and diminishing inward in subsequent bran fractions. The remaining de-branned groat, after 23% of the kernel had been removed, had the lowest avenanthramide level, less than half the avenanthramide content of the whole kernel. This trend of decreasing content with increasing removal of the outer layers was seen not only in the total avenanthramide content but, for the most part, in the levels of each of the individual avenanthramides as well.

TABLE 10

Levels of avenanthramides in whole seeds and Satake abrasion milling fractions of false malted VAO-48 oats avenanthramide content, (avenanthramide A equivalents)

| Material used | Avenanth A (ppm ± SD) | Avenanth B (ppm ± SD) | Avenanth C (ppm ± SD) | All others (ppm ± SD) | Total Avenanth (ppm ± SD) |
|---|---|---|---|---|---|
| Whole malted seed | 186.1 ± 10.6 | 324.8 ± 19.2 | 303.2 ± 22.0 | 1,056 ± 64.1 | 1,870 ± 116 |
| 0-10.7% bran fraction | 335.8 ± 11.0 | 564.7 ± 13.5 | 425.7 ± 24.1 | 2,506 ± 168 | 3,832 ± 219 |
| 10.7-20.6% bran fraction | 286.3 ± 10.1 | 468.9 ± 16.7 | 444.3 ± 23.1 | 1,744 ± 60.3 | 2,943 ± 110 |
| >20.6% de-branned groat | 117.3 ± 11.7 | 209.8 ± 15.7 | 210.9 ± 26.5 | 589.7 ± 63.8 | 1,128 ± 118 |

The trend of decreasing avenanthramide levels with increasing degree of de-branning were similar in the individual fractions collected, although the apparent degree of drop-off was less dramatic than in un-malted kernels, and the relative content of intermediate bran material and the de-branned groat were proportionally slightly higher than similar fractions in the un-malted material. Total avenanthramides accumulated in the 0-10.7% de-branning fraction reached as high as 3,832 ppm representing a 2,218% (22.2 fold) increase over a similar fraction from un-malted grain, and a 91.5 fold increase over the whole un-malted material.

If the 0-10.7% and 10.7-20.6% bran fractions were combined to form a 0-20.6% overall fraction (i.e. a 20.6% milling yield) the material has a total avenanthramide concentration of about 3,388 ppm.

These results indicate that the outer layers of the grain contain the highest levels of all the avenanthramides.

Example 9: Effects of Satake Milling of Hulless, Hairless, Non-Dormant Oat VAO 22 Oats Before and after False Malting, on the Accumulation of Avenanthramides in the Bran and De-Branned Groat Dry Milled Fractions Although the concentration of avenanthramides in the outer layers of the false malted bran is high relative to levels in whole kernels, the yield of this bran (from 7-10% of the malted kernel) is low. Due to the characteristic elongate shape and deeply defined central crease morphology of the grain, clean separation of bran and endosperm is limited and yields of bran with minimal contamination with endosperm tissue is restricted to light de-branning and low bran fraction milling yield. However, the hulless, hairless, non-dormant line VAO-22 breeding line has a short kernel and relatively shallow crease and resembles a wheat kernel in gross shape and morphology, making it much more suitable to Satake abrasion milling.

A further sample of the material used in Example 7 of VAO-22 hulless, hairless, non-dormant oat breeder's seed was used (84% germination rate after four days). The seeds were then heat treated as in Example 5. A 25 g sample was used as a control representing the un-malted seeds and stored at −20° C. until analyzed. The rest of the heat treated material was anaerobically steeped solutions at 35° C. in tap water for 18 hours. The seeds were then surface sterilized as in Example 5 and 'false malted" in the dark at 30° C. in a controlled temperature oven for four days. After malting the seeds were removed, dried to constant weight at 37° C. in a controlled temperature oven and stored at −20° C. until milled. The following Satake mill fractions were prepared as above:

0-10.1% (by weight) bran fraction 10.1-20.1% (by weight) bran fraction

>20.1% (by weight) de-branned groat

Figure 9:
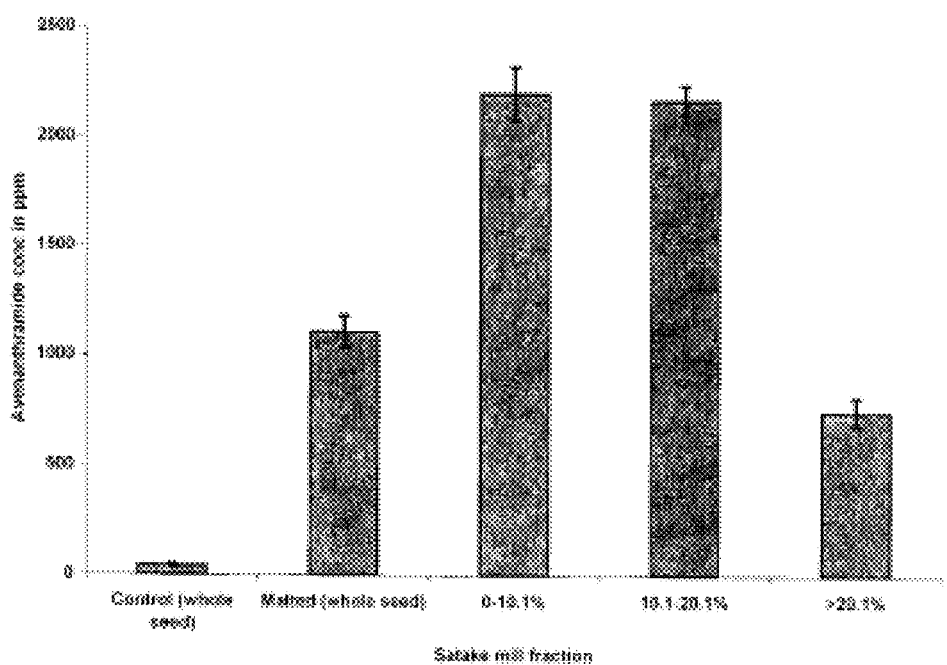
FIG. 9 illustrates distribution of total avenanthramide in kernel in another cultivar (VAO-22) after false malting as determined by Satake dry milling.

Duplicate samples of the un-milled whole malted oats and each of the mill fractions were analyzed for avenanthramide content by HPLC using Method 2 analyzed for avenanthramide content by HPLC using the third method described above (μg avenanthramide A equivalents/g dry wt=ppm avenanthramide A), and compared to un-malted material. The results are summarized in Table 11 and FIG. 9.

TABLE 11

Levels of avenanthramides in whole seeds and Satake abrasion milling fractions of false malted VAO-22 oats Avenanthramide content, (Avenanthramide A equivalents)

| Material used | Avenanth A (ppm ± SD) | Avenanth B (ppm ± SD) | Avenanth C (ppm ± SD) | All others (ppm ± SD) | Total Avenanth (ppm ± SD) |
|---|---|---|---|---|---|
| Whole un-malted seed | 7.3 ± 0.6 | 10.1 ± 0.3 | 7.7 ± 2.3 | 16.6 ± 1.6 | 41.7 ± 4.1 |
| Whole malted seed | 97.7 ± 0.6 | 162 ± 0.1 | 201.4 ± 3.5 | 647.1 ± 68.5 | 1,108 ± 73 |
| 0-10.1% bran fraction | 267.4 ± 6.6 | 246.4 ± 13.6 | 311.8 ± 19.5 | 1,372 ± 80 | 2,197 ± 120 |
| 10.1-20.1% bran fraction | 288.4 ± 9.1 | 272.0 ± 9.3 | 353.1 ± 18.8 | 1,256 ± 29 | 2,169 ± 67 |
| >20.1% de-branned groat | 93.6 ± 8.6 | 109.6 ± 8.1 | 136.5 ± 7.5 | 405.6 ± 39.0 | 745.3 ± 63 |

The total avenanthramide content of whole malted kernels shown in Table 11 increased from about 42 ppm to about 1,100 representing an increase over un-malted kernels of about 2,560% (26.6 fold). The level of avenanthramides in the 0-10.1% bran fraction increased to almost 2,200 ppm representing a 5,170% increase (52.7 fold) in avenanthramides in this material over the levels in a whole un-malted kernel. Similar increases were also seen in the 10.1-20.1% bran fraction, and if combined to form a 0-20.1% overall fraction (at 20.1% milling yield) would have a total avenanthramide concentration of about 2,183 ppm.

This is lower than comparable results shown in Table 10 using VAO-48 oats, but still represents a considerable avenanthramide increase at a milling yield of about 20%. It is evident however that this oat does not contain the rapidly decreasing trend in avenanthramide content in the comparable intermediate milling fraction observed in VAO-48 material.

It is also evident from Examples 8 and 9 that dry abrasion milling fractionation such as those generated by Satake milling of un-malted and false malted hulless, hairless oats can be used to produce bran mixtures at total avenanthramide concentrations of any desired levels and as high as about 3,000 ppm from the same degree of de-branning, to minimize changes in composition of other components such as protein, β-glucan, phytate, etc. associated with localization within the kernel.

Example 10: Accumulation of Avenanthramides in Covered, Non-Dormant Oat Varieties after a Four Day False Malting at 30° C.

Notwithstanding the economical advantages of using hulless, hairless oat varieties there are potential applications of the technology where inclusion of hulls in the final product may be justified, for example but not limited to, feed applications, industrial fractionation for non-food applications, where the removal of hulls may not prove economical.

Malting of covered oats using the technology developed in this invention will result in a product in which the hulls are either removed after malting or are still present in the product: Attempts to de-hull covered oats and removal of hairs (trichomes) by conventional de-hulling and polishing equipment results in a certain degree of mechanical damage to the kernels and subsequent complications during the malting process.

Nevertheless attempts were made to use covered oats by carefully de-hulling commercial oats and malting under the same procedures as described above. Alternatively whole covered oats were also tested as described below.

An approximately 500 g sample of covered, non-dormant oat Jordan experimental seed was used. The seeds were heat treated as in Example 5 with the hulls on and surface sterilized as in Example 5. An 80 g sub-sample was used as a control representing the un-malted seeds and stored at −20° C. until analyzed. The rest of the heat treated material was anaerobically steeped at 35° C. in tap water for 18 hours. The seeds were then surface sterilized as in Example 5 using 0.25% aqueous sodium hypochlorite solution at room temperature for 1 hour and 'false malted" in the dark at 30° C. in a controlled temperature oven for four days. After malting the seeds were removed, dried to constant weight at 37° C. in a controlled temperature oven and stored at −20° C. Duplicate samples of the whole malted oats and were analyzed for avenanthramide content by HPLC using the third method described above (μg avenanthramide A equivalents/g dry wt=ppm avenanthramide A), and compared to un-malted material.

A 1,000 g sample of covered, non-dormant oat AC Goslin was used. The seeds were heat treated as in Example 5 with the hulls on, mechanically de-hulled using a small roller de-huller to avoid damaging the kernel, and surface sterilized as in Example 5. A 25 g sub-sample was used as a control representing the unmalted seeds and stored at −20° C. until analyzed. The rest of the seed was anaerobically steeped at 35° C. in tap water for 18 hours, briefly air dried for four hours in a seed dryer at room temperature, and surface sterilized as in Example 5 using 0.25% aqueous sodium hypochlorite solution at room temperature for 1 hour The seeds were then 'false malted" in large Petri dishes (150×15 mm) on moist filter paper disks at room temperature and diffuse light for four days. After malting the seeds were removed, dried for four days in a seed dryer, and stored at −20° C. until analyzed. Duplicate samples of the whole malted oats and were analyzed for avenanthramide content by HPLC using the first method described above (μg avenanthramide A equivalents/g dry wt=ppm avenanthramide A), and compared to unmalted material.

The results are summarized in Table 12.

TABLE 12

Levels of avenanthramides in whole covered oats before and after four day false malting at 30° C.

| | Avenanthramide content (Avenanthramide A equivalents) | | | | |
|---|---|---|---|---|---|
| Material used | Avenanth A (ppm ± SD) | Avenanth B (ppm ± SD) | Avenanth C (ppm ± SD) | All others (ppm ± SD) | Total Avenanth (ppm ± SD) |
| Jordan Whole un-malted seed (hulls included) | 3.5 ± 0.1 | 3.1 ± 0.4 | 3.5 ± 0.4 | 47.0 ± 4.6 | 57.1 ± 5.4 |
| Jordan Whole malted seed (hulls included) | 19.6 ± 0.3 | 20.1 ± 0.3 | 34.9 ± 0.5 | 108.5 ± 6.3 | 183.1 ± 6.7 |
| AC Goslin Whole un-malted seed (de-hulled) | 31.7 ± 1.1 | 35.4 ± 1.3 | 33.3 ± 7.7 | 56.8 ± 3.4 | 157.2 ± 13.4 |
| AC Goslin Whole malted seed (de-hulled) | 24.1 ± 0.5 | 30.0 ± 0.7 | 31.8 ± 5.2 | 101.6 ± 3.6 | 187.4 ± 1.8 |

As can be seen in Table 12, the unmalted intact sample with hull had a total avenanthramide content of about 57 ppm. When malted for four days at 30° C., the seeds accumulated avenanthramides totaling 183.7 ppm, representing an increase of about 220% over the unmalted sample.

What is claimed is:
1. A method of increasing avenanthramide content in oat seeds, the method comprising:
(a) dry-heating the oat seeds at a temperature of 30 to 40° C. for 48 to 72 hours then at a temperature of about 70° C. for 144 to 168 hours to produce oat seeds in a state of secondary dormancy; and
(b) steeping the oat seeds from step (a) at a temperature from 4 to 40° C. for from 96 to 120 hours resulting in a false malting of the oat seeds,
wherein the false malting increases the avenanthramide concentration, without germination of the oat seeds.

2. The method according to claim 1, wherein step (a) is followed by a further step of anaerobically steeping the seeds in water at a temperature from 20 to 40° C. for from 12-18 hours prior to step (b).

3. The method according to claim 2, wherein the anaerobic steeping is in water including calcium ion.

4. The method according to claim 1, wherein the oat seeds are dormant, hulless oat seeds.

5. The method according to claim 1, wherein the increased avenanthramide concentration in the oat seeds is greater than 750 ppm on a dry basis.

6. The method according to claim 1, wherein the oat seeds are dormant with hulls, further comprising the step of de-hulling the oats.

7. The method according to claim 1, wherein the oat seeds are dried in step (a) to a final moisture content of from about 3 to 10% dry basis.

8. The method according to claim 2, wherein the oat seeds are anaerobically steeped to about 35% moisture content.

9. A method of increasing an avenanthramide concentration in oat seeds, the method comprising:
(a) dry-heating the oat seeds at a temperature of 30 to 40° C. for 48 to 72 hours then 70° C. for 144 to 168 hours to produce oat seeds in a state of secondary dormancy;
(b) anaerobically steeping the oat seeds in the state of secondary dormancy in water including calcium ion to hydrate the seeds up to about 35% moisture content; and
(c) steeping the oat seeds in the state of secondary dormancy of step (b) at a temperature of 4 to 40° C. for 96 to 120 hours, resulting in a false malting of the oat seeds,
wherein the false malting increases the avenanthramide concentration, without germination of the oat seeds.

* * * * *